United States Patent [19]

Thompson et al.

[11] 4,311,841
[45] Jan. 19, 1982

[54] PROCESS OF PREPARING HEXAHYDROPYRIMIDINES

[75] Inventors: Neil E. S. Thompson, Creve Coeur; Bernardus A. Oude Alink, St. Louis, both of Mo.

[73] Assignee: Petrolite Corporation, St. Louis, Mo.

[21] Appl. No.: 853,612

[22] Filed: Nov. 21, 1977

[51] Int. Cl.³ .................. C07D 239/72; C10L 1/22
[52] U.S. Cl. ........................................ 544/231; 44/63
[58] Field of Search .................. 260/251 A; 44/63; 544/231

[56] References Cited

U.S. PATENT DOCUMENTS 3,936,279 2/1976 Oude Alink et al. ............ 44/63
4,085,104 4/1978 Oude Alink ................. 544/231
4,085,105 4/1978 Oude Alink ................. 544/231

OTHER PUBLICATIONS

Svetozarskii, et al., Chemical Abstracts, vol. 55, 555g (1961).

Primary Examiner—Donald G. Daus
Assistant Examiner—Diana G. Rivers
Attorney, Agent, or Firm—Sidney B. Ring; Hyman F. Glass

[57] ABSTRACT

This invention relates to hexahydropyrimidines (HHP) of the formula

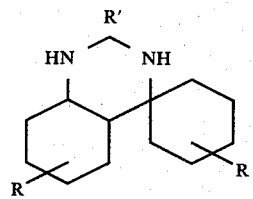

where R' is a substituted group and R is hydrogen or a substituted group; the process of preparing and the uses therefor, particularly as deterioration inhibitors in hydrocarbon fuels.

6 Claims, No Drawings

PROCESS OF PREPARING HEXAHYDROPYRIMIDINES

This invention relates to the reaction of hexahydropyrimidines of the formula

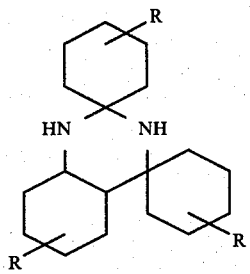

where R is hydrogen or a substituted group with an aldehyde of the formula

where R' is a substituted group to yield a hexahydropyrimidine of the formula

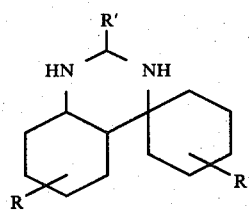

The equation may be summarized as follows:

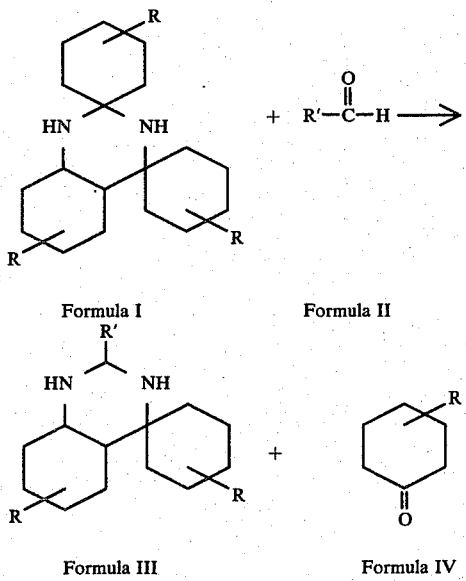

In essence, the reaction replaces the R group of the HHP with the R' of the aldehyde in the carbon position between the two amino groups (the 2 position in the ring).

In general the reaction is carried out be reacting the HHP of Formula I with the aldehyde of Formula II to yield the HHP of Formula III with the elimination of the ketone of Formula IV.

R in the above formulae is hydrogen or a substituted group for example alkyl, aryl, aralkyl, alkaryl, cycloalkyl, etc. and R' in the above formulae is a substituted group for example alkyl, aryl, aralkyl, alkaryl, cycloalkyl, as well as other groups including heterocyclic groups. Specifically R' may be $CH_3-$, $C_2H_5-$, $C_3H_7-$, $(C_2H_5)_2CH-$, isobutyl, $CH_2=CH-CH_2-$, furyl, phenyl or benzyl.

In general the reaction is carried out by reacting the HHP of Formula I with the aldehyde of Formula II at a temperature of from about 0° to 300° C., such as from about 20° to 250° C., but preferably from about 35° to 200° C., for a period of time sufficient to effect the reaction for example from about 1 to 24 hours, but preferably from about 2 to 8 hours.

In practice the reaction is carried out by employing a solvent that boils within the reaction temperature range and to continue heating until the reaction is effected.

The preparation of the HHP of Formula I is described in the following patent applications.

In Ser. No. 292,494 filed on Sept. 27, 1972, now U.S. Pat. No. 4,085,104 there is described and claimed substituted 2,3,4,5-tetrahydropyrimidines (THP)

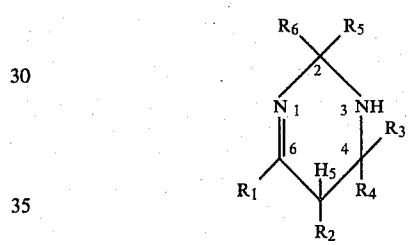

which are prepared by the following reactions:

1. The reaction of a carbonyl compound (ketone or aldehyde) with $NH_3$ (or $NH_4OH$) and a sulfur-containing catalyst.
2. The reaction of an $\alpha,\beta$-unsaturated ketone and a carbonyl compound and $NH_3$ (or $NH_4OH$) without a catalyst.
3. Reaction of an $\alpha,\beta$-unsaturated ketone, a 1-aminoalcohol and $NH_3$ (or $NH_4OH$) without a catalyst.

In the above formula, $R_1$, $R_2$, $R_3$, $R_4$, $R_5$ and $R_6$, which may be the same or different, are hydrogen or substituted group such as alkyl, aryl, cycloalkyl, alkaryl, aralkyl, heterocyclic, substituted derivatives thereof, etc. In addition R groups may be joined in a cyclic configuration which makes the THP structure a part of the substituted group.

Alkyl includes methyl, ethyl, propyl, butyl, amyl, hexyl, heptyl, octyl, nonyl, decyl, undecyl, dodecyl, tridecyl, tetradecyl, pentadecyl, hexadecyl, heptadecyl, octadecyl, escosyl, docosyl, etc. for example having about 1–25 or more carbons such as from about 1–18 carbons, but preferably about 1-12 carbons. The term "alkyl" also includes isomers of the straight chain where branching occurs.

Cycloalkyl includes cyclopentyl, cyclohexyl, etc. and derivatives thereof such as alkyl cyclohexyl, dialkylcyclohexyl, etc.

Aryl, alkaryl and aralkyl include phenyl, alkylphenyl, polyalkylphenyl, chlorophenyl, alkoxyphenyl, naphthyl, alkylnaphthyl, etc., benzyl, substituted benzyl, etc.

The joining of the R groups into a ring structure include those structures derived from reactants of the general formula

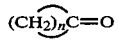

such as cyclohexanone, cyclopentanone, substituted derivatives thereof such as alkylcyclohexanone, dialkylcyclohexanone.

Ser. No. 406,544 filed Oct. 15, 1973 now U.S. Pat. No. 4,085,105 describes and claims a class of compounds which are prepared by reducing THP.

Said Ser. No. 406,544 also describes and claims a unique method of preparing HHP which comprises using a formate salt such as ammonium formate. The use of ammonium formate is unique for the following reasons:

1. In the preparation of THP from a carbonyl compound and ammonia, ammonium formate operates as a very efficient catalyst without being consumed.

2. In the preparation of HHP from THP, ammonium formate serves as a reducing agent, yielding $CO_2$ and $NH_3$ as byproducts. It is often preferred to form ammonium formate by allowing ammonia to react with formic acid present during the initial phase of the reaction. The byproducts produced in the process of preparing HHP from a carbonyl compound formic acid and ammonia, are $H_2O$, $CO_2$, and $NH_3$ and are all easily removed. The specific reaction is as follows:

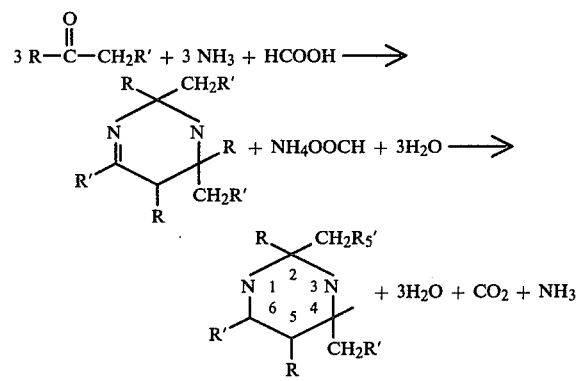

If a symmetric carbonyl compound is employed, i.e., $R=CH_2R'$ a single HHP will be produced, for example in the case of cyclohexanone, the reaction may be summarized as follows:

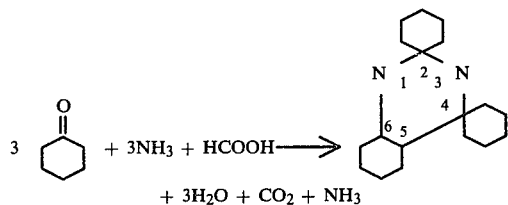

In the preferred method of Ser. No. 406,544, the carbonyl compound is reacted with ammonia in the presence of ammonium formate (or formic acid so as to form ammonium formate in situ) under pressure to keep the volatile components in the reaction mixture. The reaction is carried out at a temperature and time sufficient to produce THP, for example at a temperature of 20°–100° C. or higher, such as from 20°–55° C. for preferably from 2–18 hrs.

In general the molar ratio of carbonyl to $NH_3$ to formic acid is at least 3 to 3 to 1 but preferably 3 to 3–4 to 1.

After completion of the formation of THP, the reaction mixture is further heated, preferably under reduced pressure to remove $H_2O$ $CO_2$ and $NH_3$ at a temperature of 40°–200° C. for 0.5 to 24 hrs. to produce HHP.

The preferred carbonyl compound is cyclohexanone. Not all carbonyl compounds can be used. For example methyl ethyl ketone (MEK) when reacted with ammonia in the presence of formic acid yields a mixture of 2,4,5,6-tetramethyl-2,4-diethyl and 2,4-dimethyl-2,4,6-triethyl-2,3,4,5-tetrahydropyrimidine which upon further reaction with ammonium formate gives a mixture of dihydropyridines, a process involving deammoniation rather than reduction of the tetrahydropyrimidine moiety. However, MEK in combination with cyclohexanone yields the HHP.

Substituted cyclohexanones can also be used. Also mixtures of cyclohexanones and other ketones or aldehydes can be used so as to yield mixtures of substituted hexahydropyrimidines.

In addition the tetrahydropyrimidines can be reduced to hexahydropyrimidine by any conventional reducing technique such as, for example, with sodium-ethanol, sodiumborohydride, $LiAlH_4$, salium, bisulfite, magnesium-methanol, hydrogen catalysts such as platinum, palladium, cobalt, nickel, etc.

The following examples are presented by way of illustration and not of limitation.

EXAMPLE 1

2,2,4,4-Dipentamethylene-5,6-tetramethylene hexahydropyrimidine

A mixture of 294 grams of cyclohexanone and 51 grams of 90 percent formic acid were placed in a pressure reactor. To the mixture was added with cooling and stirring 58.6 grams of ammonia gas over a ½ hour period. The mixture was stirred for 18 hours at ambient temperature. The resulting product was subjected to a vacuum (25 mm Hg) at 60° C. and the distillate 18 grams of unreacted cyclohexanone (6 percent) and water was discarded.

The product was further heated for 3 hours at 120°–125° C. The resulting product 237.6 grams (86 percent) was identified as 2,2,4,4-dipentamethylene-5,6-tetramethylene hexahydropyrimidine, $b_{0.5}$ 153°–155° C., $C^{13}$ nuclear magnetic resonance spectrum, in agreement with a mixture of two isomers. The major component is the isomer in which the hexahydropyrimidine and cyclohexyl ring are transfused in the 5,6 position, solvent $CDCl_3$, reference T.M.S., δ in ppm.

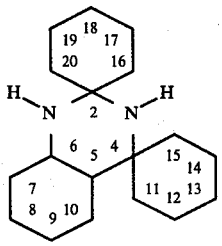

65.74 (2); 52.84 (4); 55.19 (5); 48.90 (6); 35.87 (7); 25.81* (8); 26.30* (9); 27.08* (10); 43.91 (11); 21.67** (12); 26.54* (13); 21.26 (14); 31.33 (15); 40.71 (16); 23.09** (17); 26.54* (18); 22.60 (19); 27.39* (20)

*indicates assignments are not unambiguous
**values may be interchanged

Anal. Calcd.ed for $C_{18}H_{32}N_2$; C, 78.20; H, 11.67; N, 10.14. Found: C, 77.94; H, 11.74; N, 10.08.

EXAMPLE 2

2,2,4,4-Dipentamethylene 5,6-tetramethylene 2,3,4,5-tetrahydropyrimidine

A mixture of 294 grams of cyclohexanone and 5 grams of ammonium chloride was placed in a pressure reactor. Over a ¾ hour period 38.8 grams of ammonia gas was added. After the addition was completed, the mixture was stirred for 5 hours at ambient temperature. The product was taken up in toluene and the aqueous phase which separated was discarded. The toluene solution was evaporated under diminished pressure to yield 268 grams of 2,2,4,4-dipentamethylene 5,6-tetramethylene 2,3,4,5-tetrahydropyrimidine, infrared spectrum 6.02μ (C=N) and 3.05μ (N—H), $C^{13}$ nuclear magnetic resonance spectrum, solvent $CDCl_3$, ref. T.M.S.

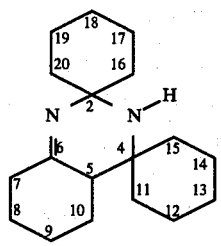

70.11 (2); 50.16 (4); 46.59 (5); 169.38 (6); 42.43 (7); 29.30 (8); 26.38 (9); 29.30 (10); 40.61 (11); 21.90* (12); 26.38 (13); 21.64* (14); 35.54 (15); 38.53 (16); 22.55* (17); 26.38 (18); 22.55* (19); 38.53 (20).

*values may be interchanged.

EXAMPLE 3

9,13,18-Trimethyl 2,2,4,4-dipentamethylene 5,6-tetramethylene 2,3,4,5-tetrahydropyrimidine A mixture of 75 grams of 4-methylcyclohexanone, 6.1 grams of ammonium chloride and 300 grams of toluene were placed in a pressure reactor. To the mixture was added with stirring 16.2 grams of ammonia gas over a 15 minute period. After the addition was completed, the mixture was stirred for 20 hours. The aqueous layer was removed and the toluene layer evaporated under diminished pressure to yield 66 grams of 9,13,18-trimethyl 2,2,4,4-dipentamethylene 5,6-tetramethylene 2,3,4,5-tetrahydropyrimidine, infrared spectrum 6.01μ (C=N), 3.08μ (N—H), $C^{13}$ nuclear magnetic resonance spectrum, solvent $CDCl_3$, reference T.M.S., δ in ppm.

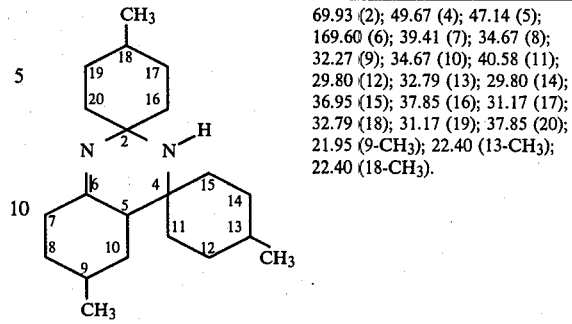

69.93 (2); 49.67 (4); 47.14 (5); 169.60 (6); 39.41 (7); 34.67 (8); 32.27 (9); 34.67 (10); 40.58 (11); 29.80 (12); 32.79 (13); 29.80 (14); 36.95 (15); 37.85 (16); 31.17 (17); 32.79 (18); 31.17 (19); 37.85 (20); 21.95 (9-$CH_3$); 22.40 (13-$CH_3$); 22.40 (18-$CH_3$).

EXAMPLE 3A

9,13,18-Trimethyl 2,2,4,4-dipentamethylene 5,6-tetramethylene hexahydropyrimidine Reduction of the compound of Example 3 was carried out as follows.

A sample of 31.6 grams of 9,13,18-trimethyl 2,2,4,4-dipentamethylene 5,6-tetramethylene 2,3,4,5-tetrahydropyrimidine, 30 grams of triethylamine and 4.6 grams of formic acid were refluxed for 16 hours. the triethylamine was distilled off under diminished pressure and 31.5 grams of 9,13,18-trimethyl 2,2,4,4-dipentamethylene 5,6-tetramethylene hexahydropyrimidine was obtained.

Anal. Calc.ed for $C_{21}H_{38}N_2$; N, 8.81. Found: N, 8.62.

EXAMPLE 4

2,2,4,4-Dipentamethylene 5,6-tetramethylene hexahydropyrimidine

A sample of 27.4 grams of 2,2,4,4-dipentamethylene 5,6-tetramethylene 2,3,4,5-tetrahydropyrimidine prepared as described in example 2, was dissolved in 50 grams of ethanol. To the ethanolic solution was added 6.9 grams of sodium metal at such a rate that a temperature of 70°-80° C. was maintained. After the addition was completed, the mixture was heated for 1 hour at 85°-95° C. The mixture was allowed to cool to ambient temperature and water was added. The organic layer which separated was taken up in toluene. The toluene solution after washing with water was evaporated under diminished pressure to yield 22.1 grams of 2,2,4,4-dipentamethylene 5,6-tetramethylene hexahydropyrimidine identical to the product described in example 1.

EXAMPLE 5

2-Isopropyl 4,4-pentamethylene 5,6-tetramethylene hexahydropyrimidine

A mixture of 137.2 grams of 2,2,4,4-dipentamethylene 5,6-tetramethylene hexahydropyrimidine, prepared as described in example 1, and 36 grams of isobutyraldehyde was heated and refluxed for 5 hours. The mixture was distilled at atmospheric pressure until a head distillation temperature of 118° C. was reached. Distillation, under diminished pressure was continued. The low boiling fraction 44.6 grams of product was identified as cyclohexanone. The fraction b.₅ 155°-170° C. was identified as 80.7 grams of 2-isopropyl 4,4-pentamethylene 5,6-tetramethylene hexahydropyrimidine, $C^{13}$ nuclear magnetic resonance spectrum showed two isomers present, with the major isomer fused in trans fashion at the 5,6 position; solvent $CDCl_3$, δ in ppm.

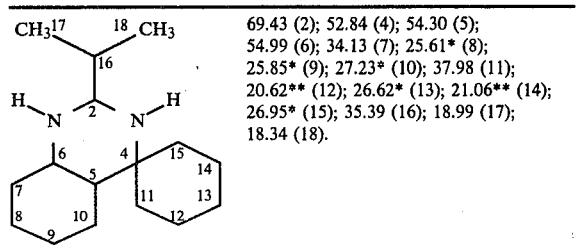

69.43 (2); 52.84 (4); 54.30 (5); 54.99 (6); 34.13 (7); 25.61* (8); 25.85* (9); 27.23* (10); 37.98 (11); 20.62** (12); 26.62* (13); 21.06** (14); 26.95* (15); 35.39 (16); 18.99 (17); 18.34 (18).

*indicates assignment are not unambiguous
**values may be interchanged.

Anal. Calc.ed for $C_{16}H_{30}N_2$; N, 11.20%. Found: N, 11.1%.

Several hexahydropyrimidines were prepared as described in example 5, from precursors as described in examples 1-4. The products of the general structure:

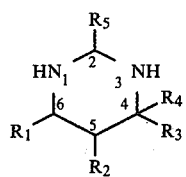

are listed in the following table:

| Ex. No. | Starting HHP Ex. | $R_1 + R_2$ | $R_3 + R_4$ | $R_5$ |
|---|---|---|---|---|
| 6 | 1,4 | $(CH_2)_4$ | $(CH_2)_5$ | $CH_3$ |
| 7 | 1,4 | $(CH_2)_4$ | $(CH_2)_5$ | $C_3H_7$ |
| 8 | 1,4 | $(CH_2)_4$ | $(CH_2)_5$ | $CH-(C_2H_5)_2$ |
| 9 | 1,4 | $(CH_2)_4$ | $(CH_2)_5$ | Phenyl |
| 10 | 1,4 | $(CH_2)_4$ | $(CH_2)_5$ | Furyl |
| 11 | 3A | $(CH_2-CH_2-CH-CH_2)$ with $CH_3$ | $(CH_2-CH_2-CH-CH_2-CH_2)$ with $CH_3$ | $CH_3$ |
| 12 | 3A | $(CH_2-CH_2-CH-CH_2)$ with $CH_3$ | $(CH_2-CH_2-CH-CH_2-CH_2)$ with $CH_3$ | $i-C_3H_7$ |
| 13 | 3A | $(CH_2-CH_2-CH-CH_2)$ with $CH_3$ | $(CH_2-CH_2-CH-CH_2-CH_2)$ with $CH_3$ | $CH_2=CH-CH_2-$ |
| 14 | 3A | $(CH_2-CH_2-CH-CH_2)$ with $CH_3$ | $(CH_2-CH_2-CH-CH_2-CH_2)$ with $CH_3$ | Phenyl |
| 15 | 3A | $(CH_2-CH-CH_2-CH)$ with $CH_3$ | $(CH_2-C-CH_2-CH_2-CH_2-CH_2)$ with $CH_3$ | $C_2H_5$ |
| 16 | 3A | $(CH_2-CH-CH_2-CH_2)$ with $CH_3$ | $(CH_2-CH-CH_2-CH_2-CH_2)$ with $CH_3$ | $-CH-(C_2H_5)_2$ |
| 17 | 3A | $(CH_2-CH-CH_2-CH_2)$ with $CH_3$ | $(CH_2-CH-CH_2-CH_2-CH_2)$ with $CH_3$ | Phenyl |
| 18 | 3A | $(CH_2-CH-CH_2-CH_2)$ with $CH_3$ | $(CH_2-CH-CH_2-CH_2-CH_2)$ with $CH_3$ | Benzyl |

USE AS FUEL ADDITIVE

As is well known, fuel oils have a tendency to deteriorate in storage and form soluble colored bodies and insoluble sludge therein. This deterioration of the oil is highly undesirable in that it causes serious adverse effects on the characteristics of the oil, particularly on the ignition and burning qualities thereof. It is also a contributory factor, along with the presence of other impurities in the oil, such as rust, dirt and moisture, in causing clogging of the equipment parts, such as screens, filters, nozzles, etc., as is explained further herein. An important economical factor is also involved in the problem of oil deterioration in storage, viz., customer resistance. Thus, customers judge the quality of an oil by its color and they oftentimes refuse to purchase highly colored oils. It will be appreciated then that since fuel oils of necessity are generally subject to considerable periods of storage prior to use, the provision of a practical means for preventing the deterioration of the fuel oil during storage would be a highly desirable and important contribution to the art.

The problem of the formation of color bodies and sludge is further aggravated because fuels, such as diesel and jet fuels, are often preheated for some time before consumption, thus introducing the additional problem of thermal instability.

We have now found that oil deterioration, with attendant formation of color and sludge in the oil, can be inhibited by employing the hexahydropyrimidine additives of this invention in the oil. In general, one employs a minor amount of the additive which is sufficient to inhibit oil deterioration with the attendant formation of color and sludge.

The amount of additive employed will vary depending on various factors, for example the particular oil to be stabilized, the conditions of storage. The stability of an oil depends largely on the nature of the crude oil from which it is made, the type of processing involved during refining, etc., and therefore some oils will require more additive to stabilize them than others. For example, caustic-treated oil will, in general, require less additive than untreated oil of similar character. In practice, one generally employs at least about 0.0001 percent (1 p.p.m.), such as from about 0.0001 to 0.1 percent (1-1000 p.p.m.), for example about 0.0002 to 0.05 percent (2–500 p.p.m.), but preferably about 0.003 to 0.03 percent (3–300 p.p.m.) based on weight of oil. Larger amounts, such as 1 percent or higher, can be employed but in general there is usually no commercial advantage in doing so.

Fuel oils in general are contemplated by the invention. The fuel oils with which this invention is especially concerned are hydrocarbon fractions having an initial boiling point of at least about 100° F. and an end point not higher than about 750° F., and boiling substantially continuously throughout their distillation range. Such fuel oils are generally known as distillate fuel oils. It will be understood, however, that this term is not restricted to straight-run distillate fractions. Thus, as is well known to those skilled in the art, the distillate fuel oils can be straight-run distillate fuel oils, catalytically or thermally cracked (including hydro-cracked) distillate fuel oils, or mixtures of straight-run distillates, naphthas and the like, with cracked distillate stocks. Moreover, such fuel oils can be treated in accordance with well known commercial methods, such as acid or caustic treatment, solvent refining, clay treatment, etc.

The distillate fuel oils are characterized by their relatively low viscosities, low pour points, and the like. The principal property which characterizes the contemplated hydrocarbon fractions, however, is the distillation range. As mentioned herein, this range will lie between about 100° F. and about 750° F. Obviously, the distillation range of each individual fuel oil will cover a narrower range falling, nevertheless, within the above-specified limits. Likewise, each fuel oil will boil substantially continuously throughout its distillation range.

Especially contemplated herein as Nos. 1, 2 and 3 fuel oils used in domestic heating and as diesel fuel oils, particularly those made up chiefly or entirely of cracked distillate stocks. The domestic heating oils generally conform to the specifications set forth in A.S.T.M. Specifications D396-48T. Specifications for diesel fuels are defined in A.S.T.M. Specifications D975-48T. Also contemplated herein are fuels for jet combustion engines. Typical jet fuels are defined in Military Specification MIL-F-5624B.

The following diesel fuel test is a standard test for diesel fuel stability and is regarded as a rapid screening test for discovering new systems, which can be used to stabilize petroleum distillate fuels.

DIESEL FUEL TEST

90 minutes at 300° F.

In the operation of a diesel engine, a portion of the fuel sent to the fuel injection system is injected and burned; the remainder is circulated back to the fuel reservoir. The injection system is located on the engine such that the fuel being returned to the reservoir is subjected to high temperatures. Consequently, diesel fuels should exhibit good thermal stability as well as good storage stability. Since the fuels used as diesel fuel are interchangeable with furnace oils, the following procedure is used to screen the thermal stability of fuel oils in general.

The test involves exposing 50 ml. samples of fuel, containing desired quantities of fuel additives, to the test where a bath is held at 300° F. and the samples are exposed for 90 minutes.

After cooling to room temperature the exposed fuel is passed through a moderately retentive filter paper and the degree of stain on the filter paper noted. The filter paper pads are compared according to a rating of 5, 4, 3, 2 or 1, where 5=worse and 1=best.

The data in the following Table shows that excellent stability was achieved in the 90-minute 300° F. diesel fuel test.

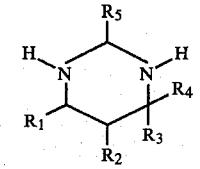

| Additive | $R_1 + R_2$ | $R_3 + R_4$ | $R_5$ |
|---|---|---|---|
| A | $(CH_2)_4$ | $(CH_2)_5$ | $i$-$C_3H_7$ |
| B | $CH_2-CH(CH_3)-CH_2-CH_2$ | $CH_2-CH(CH_3)-CH_2-CH_2-CH_2$ | $-CH-(C_2H_5)_2$ |
| C | $CH_2-CH_2-CH(CH_3)-CH_2$ | $CH_2-CH_2-CH(CH_3)-CH_2-CH_2$ | Phenyl |
| D | $(CH_2)_4$ | $(CH_2)_5$ | $n$-$C_3H_7$ |
| E | $(CH_2)_4$ | $(CH_2)_5$ | Benzyl |

90 min. 300° F. Thermal Stability Test
Whatman No. 1 Filters (Ratings are comparative: 1 = best)

| Additive | 1 at 15 ppm | 2 at 15 ppm | 3 at 30 ppm | 4 at 30 ppm | Totals |
|---|---|---|---|---|---|
| None | 5 | 5 | 5 | 5 | 20 |
| A | 1 | 2 | 1 | 2 | 6 |
| B | 2 | 2 | 1 | 2 | 7 |
| C | 3 | 2 | 2 | 2 | 9 |
| D | 2 | 1 | 2 | 2 | 7 |
| E | 3 | 3 | 4 | 3 | 13 |

Fuels are No. 2 distillate fuels, and mid-continent U.S.

Although hexahydropyrimidines are useful as fuel additives per se their performance may be enhanced by employing certain auxiliary chemical aids. Among these chemical aids are dispersants, for example acrylic polymers of copolymers which can be employed in conjunction with the hexahydropyrimides.

One such auxiliary chemical component is the copolymer derived from an acrylic ester of the formula:

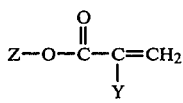

and N-vinyl-2-pyrrolidone, for example, a copolymer containing the following units:

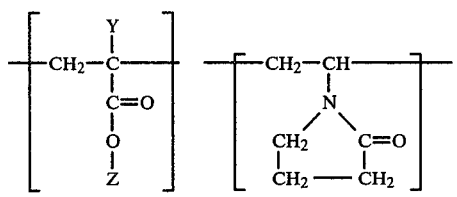

having a molecular weight for example of at least 50,000, for example 50,000–500,000, or higher, but preferably 100,000–400,000 with an optimum of 300,000–400,000 of which vinyl pyrrolidone comprises at least 1 percent by weight, of the polymer for example 1–30 percent, but preferably 3–15 percent with an optimum of 5–10 percent; where Y is hydrogen, a lower alkyl group such as methyl, ethyl, etc., Z is an hydrocarbon group having, for example, 1–30 carbon atoms, but preferably 8 to 18 carbon atoms. These polymers are preferably acrylic or methacrylic polymers, or polymers derived from both in conjunction with vinyl pyrrolidone. The Z group on the polymer, which can be the same throughout or mixed, can be octyl, nonyl, decyl, undecyl, dodecyl, tridecyl, tetradecyl, pentadecyl, octadecyl, etc. Lower alkyl groups can also be employed such as methyl, ethyl, propyl, butyl, pentyl, hexyl, heptyl, etc., but they preferably are employed as copolymers of the higher Z groups, for example a copolymer of dodecyl methacrylate and methyl acrylate, etc. The acrylic ester units may be derived from one or more acrylic type monomers and may be fully acrylic or fully methacrylic or both acrylic and methacrylic. The polymer may be random, block, graft, etc.

Also, Z may also be an alkylated aromatic group such as butyl, phenyl, amyl phenyl, etc., or a cycloaliphatic group such as cyclohexyl. Thus, non-limiting specific examples of suitable monomeric esters are: methyl acrylate, ethyl acrylate, propyl methacrylate, amyl acrylate, lauryl acrylate, cetyl acrylate, octadecyl acrylate, amyl methacrylate, lauryl methacrylate, cotyl methacrylate, octadecyl methacrylate, amylphenyl methacrylate, cyclohexyl methacrylate, etc., including the analogous acrylate or methacrylate esters. Copolymers of the above and other acrylic esters may be used, for example, a copolymer of methyl or ethyl acrylate and dodecyl methacrylate in conjunction with vinyl pyrrolidone. However, it should be understood that this description does not preclude the presence of small amounts of unesterified groups being present in the polymer, i.e., approximately 5 percent or less of where Z=H.

It should be understood, of course, that when the above compounds are polymerized, the polymerization should not be carried to such an extent as to form polymers which are insoluble or non-dispersible in the petroleum hydrocarbon used. The polymerization may be carried out by methods known to the art, such as by heating mildly in the presence of a small amount of benzoyl peroxide, but the method of polymerization is not part of this invention. For examples of acrylic-vinyl pyrrolidone copolymers see French Pat. No. 1,163,033.

| | VINYL PYRROLIDONE-ACRYLIC ESTER TYPE RESINS | | | | | |
|---|---|---|---|---|---|---|
| Ex. | Monomer 1 | Monomer 2 | Monomer 3 | Vinyl pyrrolidone, percent by wt. | Mol ratio 1:2:3 | Av. mol weight |
| 1 | Tridecyl methacrylate | Octadecyl methacrylate | | 7.5 | 1:1 | 300,000 |
| 2 | Dodecyl methacrylate | | | 10 | | |
| 3 | Dodecyl methacrylate | Butyl methacrylate | | 15 | 2:1 | 400,000 |
| 4 | Octadecyl methacrylate | | | 5 | | 450,000 |
| 5 | Tridecyl methacrylate | | | 20 | | 350,000 |
| 6 | Octadecyl methacrylate | Methyl methacrylate | | 10 | 3:1 | 500,000 |
| 7 | Dodecyl methacrylate | Ethyl methacrylate | | 5 | 4:1 | 400,000 |
| 8 | Cetyl methacrylate | Octadecyl methacrylate | Butyl methacrylate | 7.5 | 2:1:0.5 | 350,000 |

Another auxiliary chemical component is a metal deactivator for example those conveniently employed in deactivating copper, iron and other metals from hydrocarbon systems. Typical examples are those described in U.S. Pat. No. 2,282,513. Of course, one skilled in the art is aware that many other metal deactivators are known and can be employed.

The compounds employed as metal deactivators are preferably of the type of Schiff bases and may be represented by the formulae

and preferably

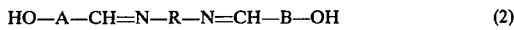

wherein A and B each represents an organic radical and preferably a hydrocarbon radical. In Formula 2A and B each preferably represents an aromatic ring or an unsaturated heterocyclic ring in which the hydroxyl radical is attached directly to a ring carbon atom ortho to the —CH=N-group. R represents an aliphatic radical having the two N atoms attached directly to different carbon atoms of the same open chain.

Typical examples of aldehyde and polyamines employed in preparing these Schiff bases include the following:

ALDEHYDES
Benzaldehyde
2-methylbenzaldehyde
3-methylbenzaldehyde
4-methylbenzaldehyde
2-methoxybenzaldehyde
4-methoxybenzaldehyde
2-naphthaldehyde
1-naphthaldehyde
4-phenylbenzaldehyde
Propionaldehyde
n-Butyraldehyde
Heptaldehyde
Aldol
2-hydroxybenzaldehyde
2-hydroxy-6-methylbenzaldehyde
2-hydroxy-3-methoxybenzaldehyde
2-4-dihydroxybenzaldehyde
2-6-dihydroxybenzaldehyde
2-hydroxynaphthaldehyde-1
1-hydroxynaphthaldehyde-2
Anthrol-2-aldehyde-1
2-hydroxyfluorene-aldehyde-1
4-hydroxydiphenyl-aldehyde-3
3-hydroxyphenanthrene-aldehyde-4
1-3-dihydroxy-2-4-dialdehyde-benzene
2-hydroxy-5-chlorobenzaldehyde
2-hydroxy-3-5-dibromobenzaldehyde
2-hydroxy-3-nitrobenzaldehyde
2-hydroxy-3-cyanobenzaldehyde
2-hydroxy-3-carboxybenzaldehyde
4-hydroxypyridine-aldehyde-3
4-hydroxyquinoline-aldehyde-3
7-hydroxyquinoline-aldehyde-8

POLYAMINES
Ethylenediamine
1-2-propylenediamine
1-3-propylenediamine
1-6-hexamethylenediamine
1-10-decamethylenediamine
Diethylenetriamine
Triethylenetetramine
Pentaerythrityletramine
1-2-diaminocyclohexane
Di-(b-aminoethyl)ether
Di-(b-aminoethyl)sulfide The ratio of hexahydropyrimidines to the metal deactivator can vary widely depending on the particular system, the fuel, etc. employed. Thus, the weight ratio of hexahydropyrimides to metal deactivator may be from about 0.1 to 20 or more, such as from about 8–15, but preferably from about 10–12.

The weight ratio of hexahydropyrimidines to the acrylic type polymer can also vary widely from about 0.1–20 or more, such as from 8–15, but preferably from about 10–12.

For ease of handling a concentrate of the additive of this invention in a solvent such as a hydrocarbon, for example in concentrations of 5–75 percent or higher, such as from 20–60, but preferably from 40–60 percent.

The additives of this invention may also be used in petroleum products to inhibit the formation of deposits on metal surfaces such as occurs in tubes, evaporators, heat exchangers, distillation and cracking equipment and the like.

We claim:

1. A process of preparing the hexahydropyrimidine of formula (I) which comprises reacting a hexahydropyrimidine of the formula (II)

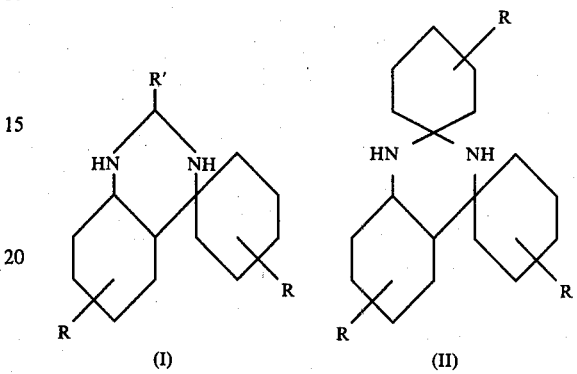

where R is hydrogen, or alkyl, aryl, aralkyl, alkaryl or cyclohexyl, with an aldehyde of the formula

where R' is a hydrocarbon group or a heterocyclic group.

2. A process of preparing a hexahydropyrimidine according to claim 1 which comprises reacting a hexahydropyrimidine of the formula

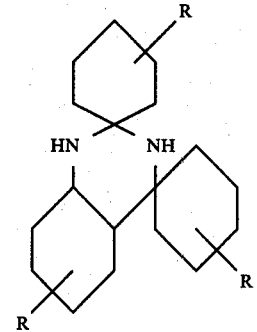

where R is hydrogen or alkyl, with an aldehyde of the formula

where R' is a hydrocarbon group selected from the group consisting of alkyl, aryl, aralkyl, alkaryl, alkenyl and cycloalkyl.

3. A process of preparing a hexahydropyrimidine according to claim 1 by reacting a hexahydropyrimidine of the formula

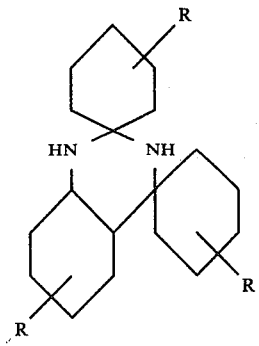

where R is hydrogen or alkyl, with an aldehyde of the formula

where R' is a heterocyclic group.

4. The process of preparing a hexahydropyrimidine according to claim 1 which comprises reacting a hexahydropyrimidine of the formula

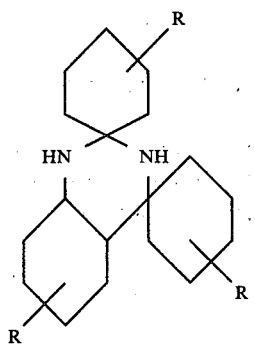

where R is hydrogen or alkyl, with an aldehyde of the formula

where R' is a hydrocarbon group which is alkyl, alkenyl, aryl, alkaryl, or aralkyl.

5. A process of preparing a hexahydropyrimidine according to claim 1 which comprises reacting a hexahydropyrimidine of the formula

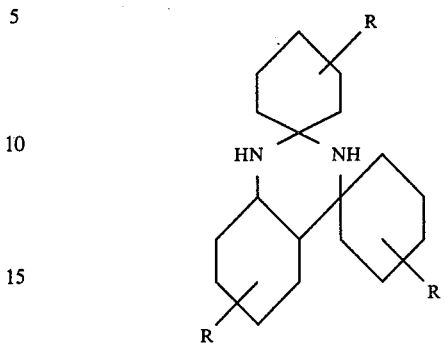

where R is a hydrogen or alkyl, with an aldehyde of the formula

where R' is furyl.

6. The process of preparing a hexahydropyrimidine according to claim 1 which comprises reacting a hexahydropyrimidine of the formula

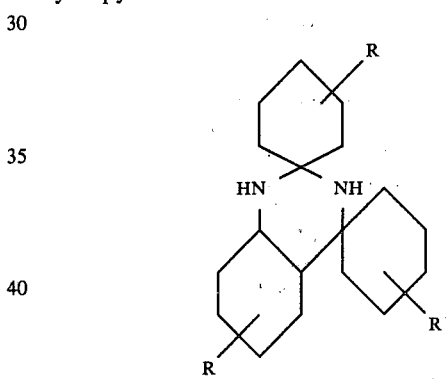

where R is hydrogen or alkyl, with an aldehyde of the formula

where R' is $CH_3-$, $C_2H_5-$, $(C_2H_5)_2CH-$, phenyl, furyl, isobutyl, $CH_2=CH-CH_2-$ or benzyl.

* * * * *